United States Patent [19]

Shimizu et al.

[11] Patent Number: 5,668,281

[45] Date of Patent: Sep. 16, 1997

[54] PROCESS FOR PREPARING TERTIARY AMINE-N-OXIDE

[75] Inventors: Shinkichi Shimizu; Nanao Watanabe; Hideki Kuranishi, all of Osaka, Japan

[73] Assignee: Koei Chemical Co., Ltd., Osaka, Japan

[21] Appl. No.: 588,881

[22] Filed: Jan. 19, 1996

[30] Foreign Application Priority Data

Jan. 23, 1995 [JP] Japan ................... 7-027488

[51] Int. Cl.$^6$ ................................ C07D 241/00

[52] U.S. Cl. ............... 544/336; 546/347; 564/297; 564/298

[58] Field of Search ............... 564/297, 298; 544/336; 546/347

[56] References Cited

U.S. PATENT DOCUMENTS

| 3,657,251 | 4/1972 | Smetana | 260/290 |
| 5,082,641 | 1/1992 | Popa et al. | 423/326 |

FOREIGN PATENT DOCUMENTS

| 0224662 | 8/1986 | European Pat. Off. . |
| 0 314 147 | 5/1989 | European Pat. Off. . |
| 0 356 918 | 3/1990 | European Pat. Off. . |
| 0 488 403 | 6/1992 | European Pat. Off. . |
| 62-181268 | 8/1987 | Japan . |

OTHER PUBLICATIONS

C.F. Koelsch et al. Some Diazine–N–Oxides—(School of Chemistry, University of Minnesota) vol. 23, pp. 1603–1606—Nov. 1958.

Yoshiro Kobayashi et al. Studies on the Reaction of Heterocyclic Compounds. XII.[1)] N–Oxidation of Diazabenzene and Diazanaphthalene[2)] — (Chem. Pharm. Bull.) vol. 22, No. 9, pp. 2097–2100—Feb. 1974).

Selective oxidation reactions over metallosilicate molecular sieves: a comparison of titanium and vanadium silicates with MEL structure. Ramaswamy et al. Microporous Materials— vol. 2, pp. 451–458, 1994.

*Primary Examiner*—Mukund J. Sham
*Assistant Examiner*—Michael Bucknum
*Attorney, Agent, or Firm*—Armstrong, Westerman, Hattori, McLeland & Naughton

[57] ABSTRACT

A process for preparing a tertiary amine-N-oxide which comprises reacting a tertiary amine with a peroxide in the presence of a catalyst comprising an oxide containing silicon and titanium atoms. According to the process of the present invention, a tertiary amine-N-oxide can be obtained in a high yield, and since the catalyst can easily be separated from the reaction mixture, the tertiary amine-N-oxide can be obtained in a high purity without the contamination by the catalyst.

9 Claims, No Drawings

PROCESS FOR PREPARING TERTIARY AMINE-N-OXIDE

BACKGROUND OF THE INVENTION

The present invention relates to a process for preparing a tertiary amine-N-oxide, and more particularly to a process for preparing a tertiary amine-N-oxide in an improved yield which comprises reacting a tertiary amine with a peroxide in the presence of a specific catalyst.

When pyridine compounds or pyrazine compounds are used as a tertiary amine in the preparation of tertiary amine-N-oxides by the reaction with hydrogen peroxide, N-oxides of pyridine compounds or N-oxides of pyrazine compounds are prepared, which are a useful compound as an intermediate for the synthesis of medicinal and agricultural compounds.

Hitherto, processes for preparing a tertiary amine-N-oxide as exemplified below are known.

As to a process for preparing N-oxides of pyrazine compounds, there are known (i) a process for preparing N-oxides of pyrazine compounds by reacting pyrazine compounds with hydrogen peroxide in acetic acid (J. Org. Chem., 23, 1603(1958)), (ii) a process for preparing N-oxides of pyrazine compounds by reacting pyrazine compounds with hydrogen peroxide in water as a solvent, using sodium tungstate as a catalyst (Chem. Pharm. Bull., 22, 2097(1974)), and (iii) a process for preparing N-oxides of pyrazine compounds by reacting pyrazine compounds with hydrogen peroxide in water as a solvent using molybdenum trioxide as a catalyst (Japanese Unexamined Patent Publication No. 181268/1987).

However, these known processes have various defects as mentioned below. In the process (i), it is necessary to use a lot of acetic acid as a solvent and, therefore, complicated steps are required to separate and recover the produced N-oxides of pyrazine compounds and acetic acid. In the process (ii), the yield of the desired compound is as low as 47%.

On the other hand, in the process (iii), the desired compound is obtained in a high yield. However, in the process (iii), there is a problem as well as in the process (ii), that is, it is difficult to easily separate the catalyst from the reaction mixture by means of the simple procedure like filtration, because the catalyst is dissolved in considerable proportion in the reaction mixture. This residual catalyst in the reaction mixture results in the contamination to the desired product separated by use of the conventional separation procedure such as removal of the solvent from the reaction mixture by distillation and subsequent crystallization from the resultant residue.

An object of the invention is to provide a process for preparing a tertiary amine-N-oxide whereby the above-mentioned problems in the known processes can be solved.

A further object of the present invention is to provide a process for preparing a tertiary amine-N-oxide in a high yield and in a high purity.

These and other objects of the present invention will become apparent from the description hereinafter.

SUMMARY OF THE INVENTION

It has now been found that a substance comprising silicon oxide and titanium oxide as chemical composition or mixture thereof is useful as a heterogeneous catalyst for the preparation of a tertiary amine-N-oxide by the reaction of a tertiary amine with a peroxide and can be easily separated from the reaction mixture by a simple procedure such as filtration, and that when a tertiary amine and a peroxide are reacted in the presence of the catalyst comprising an oxide containing silicon and titanium atoms, the tertiary amine-N-oxide can be obtained in a quite high yield.

In accordance with the present invention, there is provided a process for preparing a tertiary amine-N-oxide which comprises reacting a tertiary amine with a peroxide in the presence of a catalyst comprising an oxide containing silicon and titanium atoms.

According to the process of the present invention, a tertiary amine-N-oxide can be obtained in a quite high yield. The catalyst used in the present invention is not practically dissolved in a reaction medium and then can be easily separated from the reaction mixture by a procedure such as filtration. Therefore, the catalyst used in the process of the present invention does not contaminate the produced tertiary amine-N-oxide.

DETAILED DESCRIPTION

The catalyst comprising an oxide containing silicon and titanium atoms is used in the present invention. The catalyst comprising an oxide containing silicon and titanium atoms includes, for instance, a catalyst comprising a silicon-titanium oxide. The term "silicon-titanium oxide" as used herein means a mixed oxide of silicon and titanium and a mixture of silicon oxide and titanium oxide. Representative examples of the oxide are silicon dioxide and titanium dioxide, respectively.

The catalyst comprising a silicon-titanium oxide according to the present invention is applicable to known processes for preparing tertiary amine-N-oxides by reacting tertiary amines with peroxides such as hydrogen peroxide.

The tertiary amine used in the process of the present invention includes aromatic N-heterocyclic compounds, non-aromatic N-heterocyclic compounds, trialkylamines and trialkenylamines.

Examples of the aromatic N-heterocyclic compounds are, for instance, (1) a pyridine compound, e.g. a pyridine base such as pyridine, 2-methylpyridine, 3-methylpyridine, 4-methylpyridine, 2,3-dimethylpyridine, 2,4-dimethylpyridine, 3,5-dimethylpyridine or 2,4,6-trimethylpyridine, a cyanopyridine compound such as 2-cyanopyridine, 3-cyanopyridine or 4-cyanopyridine, a pyridinecarboxylic acid compound such as 2-pyridinecarboxylic acid, 3-pyridinecarboxylic acid or 4-pyridinecarboxylic acid, and a substituted pyridine compound wherein one or more hydrogen atoms on the pyridine nucleus of the pyridine base, the cyanopyridine compound and a pyridinecarboxylic acid compound are substituted by a halogen atom; (2) a pyrazine compound, e.g. pyrazine an alkylpyrazine compound such as 2-methylpyrazine, 2,3-dimethylpyrazine or 2,5-dimethylpyrazine, a cyanopyrazine compound such as 2-cyanopyrazine, 2-cyano-3-methylpyrazine or 2-cyano-5-methylpyrazine, a pyrazinecarboxylic acid compound such as 2-pyrazinecarboxylic acid, 3-methyl-2-pyrazinecarboxylic acid or 5-methyl-2-pyrazinecarboxylic acid, and a substituted pyrazine compound wherein one or more hydrogen atoms on the pyrazine nucleus of the pyrazine, the alkylpyrazine compound, the cyanopyrazine compound and the pyrazinecarboxylic acid compound are substituted by a halogen atom; and (3) a quinoline compound such as quinoline, 2-methylquinoline, 4-methylquinoline, 2-ethylquinoline or 4-ethylquinoline.

Examples of the non-aromatic N-heterocyclic compounds are, for instance, (1) an N-substituted morpholine compound, e.g. an N-alkylmorpholine compound such as N-methylmorpholine or N-ethylmorpholine; and (2) an N-substituted pyrrolidine compound, e.g. an N-alkylpyrrolidine compound such as N-methylpyrrolidine or N-ethylpyrrolidine.

Examples of the trialkylamines are, for instance, triethylamine, tripropylamine, tributylamine, trioctylamine, tridecylamine, trilaurylamine and tricetylamine.

Examples of the trialkenylamines are, for instance, triallylamine.

It is well known that N-oxides of pyridine compounds and N-oxides of pyrazine compounds which are prepared from pyridine compounds and pyrazine compounds, are useful as intermediates of medicinal and agricultural compounds.

Examples of the catalyst comprising a silicon-titanium oxide in the present invention are, for instance, an amorphous titanosilicate (silica-titania), a crystalline titanosilicate and the like. A particularly preferable catalyst a is crystalline titanosilicate synthesized by a hydrothermal synthesis such as a crystalline titanosilicate TS-1 having an MFI structure or a crystalline titanosilicate TS-2 having an MEL structure.

Crystalline titanosilicates having an MFI structure and an MEL structure are commercially available.

In the catalyst comprising a silicon-titanium oxide in the present invention, the atomic ratio of silicon and titanium, Si/Ti, is usually from 10 to 200.

The catalyst comprising a silicon-titanium oxide in the present invention can be prepared by various methods, using a source of a silicon oxide and a source of a titanium oxide, such as coprecipitation method, impregnation method, soaking method, ion exchange method, hydrothermal synthesis method and the like. These methods are carried out in a known manner. Examples of the source of a silicon oxide are, for instance, colloidal silica, an alkaline metal silicate such as sodium silicate or potassium silicate, a tetraalkoxysilane such as tetramethyl orthosilicate or tetraethyl orthosilicate, and the like. Examples of the source of a titanium oxide are, for instance, $TiCl_4$, $TiOCl_2$, a tetraalkoxytitanium such as tetraethyl titanate or tetraisopropyl titanate, and the like.

The catalyst in the present invention may be in various forms such as tablets, spheres, beads, granules, powder, monolith, screen, column, cylinder and the like. Preferably, the catalyst is in the form of powder.

The amount of the catalyst comprising a silicon-titanium oxide to be used is preferably from 0.1 to 5% by weight based on the tertiary amine.

Representative example of the peroxide used in the present invention is hydrogen peroxide.

With respect to the hydrogen peroxide, there can be suitably used a 30 to 35% by weight aqueous solution thereof which is commercially available.

It is suitable to use stoichiometrically 1 to 2 moles of hydrogen peroxide per mole of the tertiary amine. However, in case that the starting material is an N-heterocyclic compound having two nitrogen atoms as a ring-constituting atom, for example, pyrazine compounds and that it is intended to obtain preferentially N-oxide in which only one atom of two nitrogen atoms in the N-heterocycle is oxidized, it is preferable to use 0.4 to 1 mole of hydrogen peroxide per mole of the N-heterocyclic compound.

The process of the present invention is preferably carried out in a solvent. As the solvent used in the present invention, there can be used a solvent which can dissolve at least a part of a tertiary amine and can dissolve a desired compound to be produced but not a catalyst and which is not concerned with the reaction. Preferable examples of the solvent are, for instance, water, a mixture of water and an alcohol such as methanol or ethanol, and the like.

The amount of the solvent to be used is not particularly limited. Preferably the amount is from 1 to 10 parts by weight per 1 part by weight of a tertiary amine.

In an embodiment of the present invention, a reactor is charged with a tertiary amine, a catalyst comprising a silicon-titanium oxide and optionally a solvent. To the resulting mixture is added dropwise an aqueous solution of hydrogen peroxide over 0.5 to 10 hours with stirring at room temperature or an elevated temperature to conduct the reaction. After the completion of the addition of the aqueous solution of hydrogen peroxide, the reaction mixture is further stirred for 0 to 5 hours to complete the reaction. Thus, a tertiary amine-N-oxide can be produced in a high yield. In the above-mentioned reaction, the reaction temperature is from room temperature to 100° C., preferably from 50° to 90° C.

After the completion of the reaction, the reaction mixture is subjected to usual procedures to recover the reaction product, e.g. filtration, extraction, distillation, crystallization and the like. For example, after the reaction, the reaction mixture is cooled and potassium hydrogensulfite is added thereto to decompose the unreacted hydrogen peroxide. Then the thus treated liquid is filtered to remove the catalyst. The filtrate is concentrated and the precipitated crystals are separated by filtration. Alternatively, the filtrate is distilled. Thus, a tertiary amine-N-oxide having a high purity can be obtained. The separated catalyst can repeatedly be used for the process of the present invention.

The present invention is more specifically described and explained by means of the following Examples. It is to be understood that the present invention is not limited to the Examples.

EXAMPLE 1

A four-necked flask was charged with 30.0 g (0.379 mole) of pyridine, 1.0 g of a crystalline titanosilicate TS-1 powder having an atomic ratio of Si/Ti of 16 (commercially available from N. E. CHEMCAT CORPORATION, Japan) and 30 g of water. To the mixture was added dropwise 44.4 g (0.457 mole) of a 35% by weight aqueous solution of hydrogen peroxide over 1.7 hours at 80° C. with stirring. Thereafter the reaction mixture was kept at the same temperature for 2 hours with stirring. After the completion of the reaction, the reaction mixture was cooled to room temperature and a small amount of potassium hydrogensulfite was added thereto to decompose the unreacted hydrogen peroxide. The treated reaction mixture was filtered to remove the titanosilicate catalyst therefrom and then, the filtrate was analyzed by liquid chromatography.

Column; Intersil OD5 4.6 mm diameter×250 mm (manufactured by Gasukuro Kogyou Inc.)

Eluent: Water/Methanol (95/5 by volume) where water (1 l) contains $KH_2PO_4$ (6.8 g), $C_8H_{17}SO_3Na$ (1.08 g) and 85% $H_3PO_4$ (1 ml).

Flow rate: 0.5 ml/min

Detection: UV 265 nm

It was found that 36.1 g (0.379 mole) of pyridine-N-oxide was produced. The yield was 100%.

EXAMPLE 2

In a four-necked flask were placed 30.1 g (0.376 mole) of pyrazine, 1.0 g of the same crystalline titanosilicate catalyst as used in Example 1 and 10.1 g of water. To the mixture was added dropwise 18.5 g (0.190 mole) of a 35% by weight aqueous solution of hydrogen peroxide over 1.25 hours at 80° C. with stirring. The reaction mixture was further kept at the same temperature for 2 hours with stirring. After the completion of the reaction, the reaction mixture was cooled to room temperature and filtered to remove the catalyst therefrom. The filtrate was analyzed by liquid chromatography in the same manner as in Example 1. It was found that 17.5 g (0.182 mole) of pyrazine-N-oxide was produced. The yield was 95.8% on the hydrogen peroxide basis. It was also found that 0.25 g (0.0022 mole) of pyrazine-N, N'-dioxide was produced.

In addition to the ingredients used in the Examples, other ingredients can be used in the Examples as set forth in the specification to obtain substantially the same results.

What is claimed is:

1. A process for preparing a tertiary amine-N-oxide which comprises reacting a tertiary amine with a peroxide in the presence of a catalyst comprising a mixed oxide of silicon and titanium wherein the atomic ratio of silicon to titanium, Si/Ti, is from 10 to 200.

2. The process of claim 1, wherein said catalyst is a crystalline titanosilicate.

3. The process of claim 1, wherein said catalyst is an amorphous titanosilicate.

4. The process of claim 1 wherein said tertiary amine is a member selected from the group consisting of an aromatic N-heterocyclic compound, a non-aromatic N-heterocyclic compound, a trialkylamine and a trialkenylamine.

5. The process of claim 1, wherein said tertiary amine is an aromatic N-heterocyclic compound.

6. The process of claim 1, wherein said tertiary amine is a pyridine compound.

7. The process of claim 1, wherein said tertiary amine is a pyrazine compound.

8. The process of claim 1, wherein said catalyst is used in an amount of 1 to 2 moles per mole of the tertiary amine.

9. The process of claim 1, wherein said peroxide is hydrogen peroxide.

* * * * *